United States Patent
Bouwstra et al.

(10) Patent No.: US 7,670,839 B2
(45) Date of Patent: Mar. 2, 2010

(54) PROCESS FOR COATING CELL-CULTURE SUPPORT

(75) Inventors: Jan Bastiaan Bouwstra, Bilthoven (NL); Andries Johannes Jozef Van Es, Dorst (NL); Yuzo Toda, Asaka (JP)

(73) Assignee: Fuji Film Manufacturing Europe B.V., Tilburg (NL)

( * ) Notice: Subject to any disclaimer, the term of this patent is extended or adjusted under 35 U.S.C. 154(b) by 352 days.

(21) Appl. No.: 10/540,167

(22) PCT Filed: Dec. 23, 2003

(86) PCT No.: PCT/NL03/00922

§ 371 (c)(1),
(2), (4) Date: Jan. 25, 2006

(87) PCT Pub. No.: WO2004/056976

PCT Pub. Date: Jul. 8, 2004

(65) Prior Publication Data

US 2007/0004034 A1    Jan. 4, 2007

(30) Foreign Application Priority Data

Dec. 23, 2002   (EP) ................... 02080539

(51) Int. Cl.
C12N 5/00 (2006.01)
C07K 14/00 (2006.01)
(52) U.S. Cl. ............................ 435/402; 530/350; 514/2
(58) Field of Classification Search ....................... None
See application file for complete search history.

(56) References Cited

U.S. PATENT DOCUMENTS 4,994,388 A      2/1991   Hillegas et al.
5,906,940 A  *   5/1999   Wandrey et al. ............ 435/402

FOREIGN PATENT DOCUMENTS

EP          0 967 226       12/1999
WO          WO 91/07485     5/1991
WO          WO 01/34646     5/2001

* cited by examiner

*Primary Examiner*—Anand U Desai
(74) *Attorney, Agent, or Firm*—K & L Gates LLP

(57) ABSTRACT

The invention relates to a support for culturing cells, in particular to microcarriers coated with gelatine or gelatine-like proteins. Such microcarriers serve as support for culturing anchorage dependent cells. In particular the invention relates to a process for the preparation of a cell culture support comprising the step of coating a microcarrier bead with gelatine or gelatine-like protein, said gelatine or gelatine-like protein having a molecular weight of about 40 kDa to about 200 kDa.

15 Claims, No Drawings pagenum_skip

PROCESS FOR COATING CELL-CULTURE SUPPORT

FIELD OF THE INVENTION

The present invention relates to a support for culturing cells, in particular to microcarriers coated with gelatine or gelatine-like proteins. Such microcarriers serve as support for culturing anchorage dependent cells.

BACKGROUND OF THE INVENTION

Cell culture of animal cells, in particular mammalian cells, is important for the production of many important (genetically engineered) biological materials such as vaccines, enzymes, hormones and antibodies. The majority of animal cells are anchorage-dependent and require attachment to a surface for their survival and growth.

Routinely, anchorage-dependent cells have been cultivated on the walls of for instance tissue culture flasks and roller bottles. As the necessity has developed to provide large amounts of certain antiviral vaccines, genetically engineered proteins, and other cell-derived products, improvements have been made to develop new systems for larger scale production of cells.

One such an improvement started with the development of microcarriers in 1967 by Van Wezel (Van Wezel, A. L. *Nature* 216:64-65 (1967)). Van Wezel made microcarriers composed of cross-linked dextran beads charged with tertiary amine groups (DEAE). He demonstrated the attachment and growth of cells on these positively charged DEAE-dextran beads suspended in culture media in a stirred vessel. Thus, in microcarrier cell cultures cells grow as monolayers on small spheres which are in suspension. By using microcarriers it is possible to achieve yields of several million cells per millilitre. Over the years various types of microcarriers have been developed. Crosslinked dextran, like the first microcarriers, is still the most popular bead material.

Some advantages of microcarrier cultures over other methods of large-scale cultivation are: i) high surface area to volume ratio can be achieved which can be varied by changing the microcarrier concentration leading to high cell densities per unit volume with a potential for obtaining highly concentrated cell products; ii) cell propagation can be carried out in a single high productivity vessel instead of using many low productivity units, thus achieving a better utilisation and a considerable saving of medium; iii) since the microcarrier culture is well mixed, it is easy to monitor and control different environmental conditions such as pH, $pO_2$, $pCO_2$ etc.; iv) cell sampling is easy; v) since the beads settle down easily, cell harvesting and downstream processing of products is easy; vi) microcarrier cultures can be relatively easily scaled up using conventional equipment like fermenters that have been suitably modified.

When developing further improvements the following requirements for an optimum microcarrier should be met: i) the surface properties of the beads should be such that cells can adhere and proliferate rapidly, preferably the contour should be even; ii) the density of the beads should be slightly more than that of the culture medium, so as to facilitate easy separation; conventional culture media are aqueous in nature and have densities ranging from 1.03-1.09 g/cc, however, the density should not exceed a certain limit the optimum range being 1.03-1.045 g/ml; gentle stirring, which will not harm the shear-sensitive cells, should be sufficient to keep them in suspension, if the beads settle down cell growth will be prevented; iii) the size-distribution of the beads should be narrow so that an even suspension of all microcarriers is achieved and cells attain confluency at approximately the same time; also, clustering of microcarriers in solution should be prevented; iv) the optical properties should enable easy microscopic observation; v) they should be non-toxic not only for the survival and good growth of the cells but also for cell culture products that are used for veterinary or clinical purposes; vi) the matrix of the beads should be such that collisions, which occur during stirring of the culture, do not cause fragmentation of the beads.

An important modification in the development of improved microcarriers is the coating of core particles with collagen. The advantage of using collagen is that it is a promoter for both cell attachment and cell growth. In addition cells can be easily detached by proteolytic enzymes. Several collagen-coated micorcarriers are commercially available such as for instance SoloHill™ collagen-coated microcarriers and Cytodex 3™ from Amersham Biosciences. There is however a strong need for further improvements of microcarriers to meet the requirements for optimum microcarriers outlined above.

A process for the preparation of collagen coated microcarriers is described in U.S. Pat. No. 4,994,388. Providing a core bead with a collagen coating is performed in two steps: coating and fixing. The core beads are suspended in an acidic, aqueous collagen solution (0.01-0.1N acetic acid), and the solution is evaporated to dryness. The dry, collagen-coated beads are then suspended in a solution which contains a protein crosslinking agent such as glutaraldehyde, thus crosslinking the collagen coating. Alternatively, the core beads wetted with the collagen solution are not dried entirely before the start of the fixing step.

Whereas in the art in this field often the term collagen or denatured collagen is used, throughout the rest of this description the term gelatine or gelatine-like protein will be used. The term gelatine more truly reflects the appearance of the protein, being a single polypeptide chain, whereas collagen normally is used to describe a structure of three polypeptide chains oriented in a helical bundle.

SUMMARY OF THE INVENTION

It is an object of the invention to provide an improved process for coating a microcarrier with gelatine or gelatine-like proteins allowing clustering between microcarrier particles in cell cultures to be prevented.

It is a further object to provide gelatine-coated microcarriers or micorcarriers coated with gelatine-like proteins with improved properties for use in large scale cell cultures.

A further object is to develop new recombinant gelatines with improved functionality for microcarriers.

The present invention surprisingly meets these objects with a process for the preparation of a cell culture support comprising the step of coating a core bead with gelatine or gelatine-like protein, said gelatine or gelatine-like protein having a selected molecular weight of about 40 kDa to about 200 kDa.

DETAILED DESCIPTION OF THE INVENTION

In the process of the invention a gelatine or gelatine-like protein is used of about 40 kDa to about 200 kDa to coat a core bead resulting in a cell culture support in the form of a microcarrier.

The selected molecular weight range of the gelatine or gelatine-like protein offers striking advantages in the process of preparing the microcarriers and provides the resulting microcarriers with advantageous properties. A key problem in the coating process is the clumping together of beads. In particular such clumping reduces the available surface area for cell attachment and disturbs the size distribution of the microcarriers rendering them unusable. Gelatine isolated from natural sources has a wide molecular weight size distribution, ranging from peptide fragments smaller than 20 kD up to macropolymers with molecular weights larger than 400 kD.

We found that the relatively small fraction of high MW gelatine polymer molecules within a natural gelatine batch is to a large extent responsible for the clumping together of beads during the microcarrier production process. We concluded that when such a gelatine polymer with high molecular weight adheres to a core bead, a part of the peptide chain may point away from the surface of the core bead and as such be an anchor for other beads and thus induce coagulation.

It is therefore preferred according to the present invention to coat core beads with gelatine having a molecular weight of less than 200 kDa, more preferably less than 150 kDa, most preferably less than 100 kDa.

We found furthermore that the small MW fraction of a natural gelatine shows unfavourable microcarrier coating characteristics. This small MW fraction showed a lower adsorption force to the microcarrier beads, and, thus, when not being adsorbed it promotes microcarrier clumping after the chemical crosslinking step. Additionally, in case of the use of lower concentrations of the gelatine in the microcarrier coating process to prevent clumping, the small MW fraction is at first instance adsorbed to the microcarrier but has the unfavourable characteristic of entering the small pores of a microcarrier porous core beads, thereby not contributing to the attachment of the cells on the microcarrier during the cell culture step. Thus, the molecular weight of the gelatine should be high enough to perform the actual coating process effectively resulting in efficient coating, to prevent clumping of the core beads and to prevent loss of the gelatine. Thus the molecular weight of the gelatine should be higher than 40 kDa, preferably higher than 60 kDa, most preferably higher than 70 kDa.

Preferably the molecular weight of the gelatine or gelatine-like protein that is used is uniform, with more than 75%, preferably more than 85%, more preferably more than 95% or even at least 98% of the gelatine or gelatine-like protein having a uniform MW within 2% from the selected molecular weight.

Preferably a recombinant production method is used to obtain such a uniform molecular weight. An advantage of recombinant gelatine or gelatine-like protein is the constant composition of the material in contrast to isolated gelatine from natural sources which always will have some variation.

It is known that prions and other viruses could be part of a traditional gelatine batch. However, the risks are so far not recognised fully, as still traditional gelatines are applied for microcarrier applications for cell culture use. However, we found that by coating the core beads of a microcarrier with traditional gelatines, potentially present prions will not be chemically cross-linked to the beads. A consequence of this surprising and new finding is that prions, if present in a traditional gelatine batch, will be mixed with the cell culture products, aimed for human use. To prevent any risk of a contamination with prions such as BSE, the preferred gelatine for microcarrier applications is a recombinant gelatine.

By selecting a molecular weight, within the range of the invention the viscosity of the gelatine or gelatine-like protein coating solution can be accurately controlled. Complete or, more important, partial gelling of such a gelatine solution can be prevented while being able to select a high as possible concentration of the gelatine or gelatine-like protein. The uniform gelatine or gelatine-like protein ensures a process of identically coated microcarriers. The uniform coating process allows the use of a minimum amount of gelatine or gelatine-like protein and the use of a minimum volume of gelatine or gelatine-like protein coating solution. All this results in a far more efficient coating process than that is known in the art.

In one embodiment of the invention non-porous core beads are coated with gelatine or gelatine-like protein. Suitably non-porous core beads are made of polystyrene or glass. Other suitable non-porous materials are known to those skilled in the art.

A particular advantageous embodiment is the process of the invention wherein porous core beads, such as beads from modified dextran or cross-linked cellulose, or (porous) polystyrene, in particular DEAE-dextran, are coated with gelatine or gelatine-like protein. Other suitable porous materials are known to those skilled in the art, and include e.g. other chemically modified or non-modified polysaccharides. The lower molecular weight limit prevents that gelatine or gelatine-like protein enters the pores of the porous core beads thereby preventing inefficient coating of the beads and unnecessary loss of gelatine or gelatine-like protein.

In a further preferred embodiment the gelatine or gelatine-like protein is in essence free of hydroxyproline residues. Hydroxylation is a requirement for the formation of triple helices in collagen and plays a role in gelation of gelatine.

In yet a further embodiment the process of the invention comprises the step of immobilising the gelatine or gelatine-like protein on the microcarrier. Such inmobilisation methods are known per se. A preferred method is crosslinking of the gelatine or gelatine-like protein with glutaraldehyde as described in U.S. Pat. No. 4,994,388.

Processes for coating core beads with gelatines (or collagens) are known per se. For instance the process described in U.S. Pat. No. 4,994,388 may be used. In short a core bead is coated with a gelatine in two steps: coating and fixing. The core beads are suspended in an acidic, aqueous collagen solution (0.01-0.1N acetic acid), and the solution is evaporated to dryness. The dry, gelatine-coated beads are then suspended in a solution which contains a protein cross-linking agent such as glutaraldehyde, thus crosslinking the gelatine coating. Alternatively, the core beads wetted with the gelatine solution are not dried entirely before the start of the fixing step. Variations in coating conditions and alternative coating processes are well within the competence of those skilled in the art.

It is known in the art that incorporation of positive charges onto gelatine microcarriers greatly improves the rate of cell attachment to these microcarriers, see U.S. Pat. No. 5,512,474. Recombinant production of gelatines allows easy manipulation of the number of positively charged amino acids, meaning positively charged at the pH of the cell culture, in the produced protein. In particular arginine, lysine and histidine carry positive charges. It is well within the reach of the skilled person to design a gelatine with a net positive charge at the pH of the particular cell culture of interest. Cells are normally cultured at a pH of 7-7.5. Thus in a further embodiment of the invention a gelatine or gelatine-like protein is used that has a net positive charge at pH 7-7.5. Preferably the net positive charge is +2, +3, +4, +5, +10 or higher.

Also chemical modification can be used to control the number of positively charged amino acids in a protein. Methods are described in The Practice of Peptide Synthesis, M. Bodansky, Springer-Verlag, Berlin 1984.

A natural gelatine molecule in its primary amino acid sequence basically consists of repeats of Gly-Xaa-Yaa triplets, thus approximately one third of the total number of amino acids is a glycine. The molecular weight of gelatine is typically large, values of the molecular weight vary from 10,000 to 300,000 Dalton and higher. The fraction very high molecular weight may be relatively small, but is very detrimental in the coating process in view of the disadvantageous clumping together of beads. The main fraction of natural gelatine molecules has a molecular weight around 90,000 Dalton. The average molecular weight is higher than 90,000 Dalton.

Furthermore, characteristic for gelatine is the unusual high content of proline residues. Even more characteristic is that in natural gelatine a number of the proline residues is hydroxylated. Most prominent site of hydroxylation is the 4-position resulting in the presence in the gelatine molecule of the unusual amino acid 4-hydroxyproline. In a triplet 4-hydroxyproline is always found in the Yaa position. Very few proline residues are hydroxylated at the 3 position. In contrast with 4-hydroxyproline, 3-hydroxyproline is always found at the carboxyl side of a glycine residue, thus in the Xaa position in a triplet. Different enzymes are responsible for the formation of 3- or 4-hydroxyproline.

Based on known amino acid compositions, it is estimated that in a gelatine molecule derived from a mammal, approximately 22% of the amino acids are a proline or a hydroxyproline residue. However lower contents of proline and hydroxyproline are found in fish, in particular cold water fish. A rough estimate is that proline and hydroxyproline residues are present in approximately equal amounts, thus in a gelatine molecule derived from a mammal approximately 11% of the amino acids are prolines and approximately 11% are hydroxyprolines. As substantially all hydroxyproline is found in the Yaa position, it is estimated that approximately one third of all triplets in a gelatine molecule comprise a hydroxyproline. The presence of the hydroxyproline residues is responsible for the fact that a gelatine molecule in its secondary structure can adopt a helical conformation. Thus, it is preferred that the gelatines to be used according to the invention contain less than 5%, preferably less than 3%, most preferably less than 1% of hydroxyproline residues, be it 3- or 4-hydroxyprolines.

Gelatine-like proteins for use according to the invention are understood as proteins in which at least 5% of the total number of amino acids is a proline residue. By this percentage the gelatine-like characteristics, for the purpose of this invention not being defined as the gelling property but as the absence of non-preferred 3-dimensional globular domains, is assured. Preferably in the gelatine-like protein at least 10%, more preferably at least 15% of the total number of amino acids is a proline residue. The lower the proline content of a protein the more the distribution of the proline residues in the protein becomes relevant. Thus in a protein in which 5% of the total number of amino acids is a proline residue, these residues are preferably evenly distributed. In designing a suitable protein the skilled person, for instance with the aid of computer modelling systems, will be able to design sequences comprising proline residues which will not give rise to globular domains. In order to prevent the formation of globular domains as a guideline the gelatine-like protein for use in the invention preferably should not comprise stretches of more than 20 amino acids without a proline residue.

One gelatine-like protein for use according to the invention can consist of at least 95% of Gly-Xaa-Yaa triplets and can contain at least 15% of proline residues and less than 5% of hydroxyproline residues. The molecular weight distribution of the protein can show a maximum between 40 kDa and 200 kDa, at least 75% of the protein molecules having a molecular weight within 2% of the maximum.

A predominant feature of gelatines is the presence of Gly-Xaa-Yaa triplets. Such triplets are preferably also present in the gelatine-like proteins used in the invention. It is however possible to design a protein in which Gly-Xaa-Yaa triplets or stretches of Gly-Xaa-Yaa triplets are separated by one or more amino acids. In such a gelatine-like protein having 'interrupted' triplets or stretches of triplets the definition of gelatine-like characteristics given above is useful. In relation to a protein consisting completely of Gly-Xaa-Yaa triplets the definition given above of a gelatine-like protein for use in the invention can be described as a protein in which at least 15% of the triplets comprise a proline residue. Preferably such a gelatine-like protein does not comprise a stretch of more than 6 triplets without a proline residue. It is preferred a gelatine-like protein for use in the invention comprises stretches of at least 10, preferably at least 20, more preferably more than 30 consecutive repeats of Gly-Xaa-Yaa triplets.

The gelatine-like proteins for use according to the invention can be produced by recombinant methods as disclosed in EP-A-0926543 and EP-A-1014176. For enablement of the production and purification of gelatine-like proteins that can be suitably used in composition according to the invention specific reference is made to the examples in EP-A-0926543 and EP-A-1014176. Thus the gelatine-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* offers an example of a very suitable expression system. As disclosed in EP-A-0926543 and EP-A-1014176 specifically *Pichia pastoris* is used as expression system. In one embodiment the micro-organism is also transformed to include a gene for expression of prolyl-4-hydroxylase1. In embodiment the micro-organism is free of active post-translational processing mechanism such as in particular hydroxylation of proline.

The size of the beads may vary from 50 μm to 500 μm. Typical mean microcarrier bead sizes are about 100, about 150 or about 200 μm in physiological saline. Size ranges with at least 90% of the beads lying within the range may vary from 80-120 μm, 100-150 μm, 125-175 μm or 150-200 μm.

A wide range of cells may be cultured on microcarriers. For instance, cells from invertebrates, from fish, birds and cells of mammalian origin may be cultivated on microcarriers. Transformed and normal cell lines, fibroblastic and epithelial cells and even genetically engineered cells may be cultivated on microcarriers for various biologicals such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation as well. Cells growing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic examinations or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labelled compounds.

Microcarriers may also be used for the depletion of macrophages from a population of spleen cells. DEAE-dextran microcarriers can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers.

Due to the large surface area to volume ratio provided by microcarriers, they can successfully be used for a variety of biologicals on a laboratory as well as an industrial scale of for instance even 4000 litres.

Large scale production of expressed products can be accomplished with gelatine-coated microcarriers. Loading of microcarriers in production scale bioreactors is generally 20 g/l, but may be increased up to 40 g/l. Microcarriers may be used in batch and perfusion systems, in stirred cultures, and wave bioreactors, as well as to increase the surface area of traditional stationary monolayers and roller cultures

EXAMPLES

Example 1

Preparation of Microcarriers Beads

Human recombinant gelatine-like polypeptide Hu-3 with a molecular weight of approximately 54 kDa was produced by recombinant methods as disclosed in EP-A-0926543 or EP-A-1014176.

```
Amino acid sequence of Hu-3 (SEQ ID NO 1):
  1 G P P G E P G P T G L P G P P G E R G G P G S R G F P G A D

31 G V A G P K G P A G E R G S P G P A G P K G S P G E A G R P

61 G E A G L P G A K G L T G S P G S P G P D G K T G P P G P A

91 G Q D G R P G P P G P P G A R G Q A G V M G F P G P K G A A

121 G E P G K A G E R G V P G P P G A V G P A G K D G E A G A Q

151 G P P G P A G P A G E R G E Q G P A G S P G F Q G L P G P A

181 G P P G E A G K P G E Q G V P G D L G A P G P S G P A G E P

211 G P T G L P G P P G E R G G P G S R G F P G A D G V A G P K

241 G P A G E R G S P G P A G P K G S P G E A G R P G E A G L P

271 G A K G L T G S P G S P G P D G K T G P P G P A G Q D G R P

301 G P P G P P G A R G Q A G V M G F P G P K G A A G E P G K A

331 G E R G V P G P P G A V G P A G K D G E A G A Q G P P G P A

361 G P A G E R G E Q G P A G S P G F Q G L P G P A G P P G E A

391 G K P G E Q G V P G D L G A P G P S G P A G E P G P T G L P

421 G P P G E R G G P G S R G F P G A D G V A G P K G P A G E R

451 G S P G P A G P K G S P G E A G R P G E A G L P G A K G L T

481 G S P G S P G P D G K T G P P G P A G Q D G R P G P P G P P

511 G A R G Q A G V M G F P G P K G A A G E P G K A G E R G V P

541 G P P G A V G P A G K D G E A G A Q G P P G P A G P A G E R

571 G E Q G P A G S P G F Q G L P G P A G P P G E A G K P G E Q

601 G V P G D L G A P G P S G P A G G
```

Polystyrene beads with an average diameter of 100 micrometers are used. The heterobifunctional crosslinking agent, BBA-EAC-NOS, is used to covalently immobilise gelatine onto polystyrene beads. The BBA-EAC-NOS is added to the polystyrene beads and allowed to adsorb. Next, gelatine Hu-3 is added and is allowed to react with the NOS synthetic polymer to produce covalent coupling to the spacer. Then the beads are photoactivated (at 320 nm) to covalently immobilise the spacer (and covalently coupled gelatine) to the polystyrene beads. Finally, loosely adherent gelatine is removed by overnight washing with the mild detergent Tween 20 in phosphate buffered saline (pH 7.2).

Example 2

Cell Attachment and Cell Culture Protocol for Gelatine or Gelatine-like Protein Coated Microcarriers Practical information on how to carry out cell cultures using microcarriers can be found in the handbook "Microcarrier cell culture—principles and methods" which can be obtained from Amersham Biosciences, code no. 18-1140-62.

The following is a protocol which can be used to make a 200 ml suspension culture in a spinner flask. Cell cultures at bead loadings of 5-40 grams per litre have been demonstrated successfully. Twenty (20) grams per litre is suggested as a starting point. Therefore this 200 ml culture will require 4 grams of beads. Except for weighing and suspending the microcarrier beads, aseptic techniques should be used throughout the protocol.*

1. Siliconising glassware will prevent cell attachment to the treated glassware. We use Prosil-28 to siliconise but any other commercially available agent is acceptable. Clean, siliconise and autoclave all the glassware and pipettes.

2. Suspend 4 grams of microcarrier beads in deionised or distilled water or calcium and magnesium free phosphate buffered saline solution (CMF-PBS) and autoclave at 121° C. or 131° C. for 15 minutes on the liquid cycle.

3. Discard the autoclaving liquid and rinse the 4 grams of beads in a small amount of media. The type of media used should be the same as was used in a monolayer culture and the same as this 200 ml culture. The intent is to both rinse away the autoclaving liquid and to condition the beads with the media. Multiple rinses are commonly used and will eliminate debris or precipitants if present.

4. Place the microcarrier/media solution in the $CO_2$ incubator for a minimum of 30 minutes. Discard this media and resuspend the beads in 90 ml of fresh warm media.

5. The cell inoculum is generally $1 \times 10^5$ cells/ml. For a total culture volume of 200 ml culture, $2 \times 10^7$ cells are needed. Add the cells to the warm, microcarrier/media bead suspension and add enough warm media to make 100 ml. (The cells should be in the log phase for optimum attachment and growth.) The attachment phase of the spinner culture should occur at ½ volume to facilitate cell to bead interactions. Stir as slowly as possible while preventing the bead/cell slurry from forming a static layer on the bottom of the stir flask. For fastidious cells which attach more slowly, an intermittent stirring protocol may be required. If cells are slow to attach and spread in monolayer, they will be slow to attach on the microcarriers.

6. Stir the incubated spinner flask at 18-21 rpm for a minimum of 6 hours. Frequently, the spinner flask runs overnight (i.e., 12-14 hours is often used). If your system allows intermittent stirring, use it. We find it useful to set the stir cycle at 1 minute on and 20-30 minutes off. Bring the volume to 200 ml with fresh, warm media.

7. Maintain the cells as required by their growth and metabolism. Generally, one half media exchange is needed every second day. This cell attachment protocol has been used successfully with a variety of cell lines. We have successfully used Bellco, Corning, Kontes, Techne and Wheaton stirring systems and expect other microcarrier stirrers to be acceptable also.

* Bead hydration not required.

---

The invention claimed is:

1. A process for the preparation of a cell culture support comprising a microcarrier bead coated with gelatine-like protein, the process comprising the step of coating a microcarrier bead with gelatine-like protein, said gelatine-like protein having a molecular weight of from about 40 kDa to about 200 kDa, wherein at least 95% of the amino acid residues of the gelatine-like protein consists of Gly-Xaa-Yaa triplets, wherein the gelatine-like protein comprises at least 15% of proline residues and less than 5% of hydroxyproline residues, wherein 3-dimensional globular domains are absent from the gelatine-like protein and wherein more than 75% of the gelatine-like protein has a uniform molecular weight.

2. The process according to claim 1, wherein the microcarrier bead is a non-porous bead.

3. The process according to claim 1, wherein the microcarrier bead is a porous bead.

4. The process according to claim 1, wherein the gelatine-like protein has a molecular weight of more than 60 kDa.

5. The process according to claim 1, wherein the gelatine-like protein has a molecular weight of less than about 150 kDa.

6. The process according to claim 1, further comprising the step of immobilizing the gelatine-like protein on the microcarrier.

7. The process according to claim 1, wherein more than 75% of the gelatine-like protein has a molecular weight within 2% of a selected molecular weight.

8. The process according to claim 1, wherein the gelatine-like protein is recombinantly produced.

9. The process according to claim 1, wherein the gelatine-like protein has a net positive charge at pH 7-7.5.

10. The process according to claim 1, wherein the gelatine-like protein comprises a single polypeptide chain.

11. The process according to claim 1, wherein the gelatine-like protein is free of hydroxyproline residues.

12. The process according to claim 1, wherein the microcarrier beads comprise a material selected from the group consisting of modified dextran, cross-linked cellulose, porous polystyrene, diethylaminoethyldextran, chemically modified polysaccharides and unmodified polysaccharides and optionally at least 90% of the beads have a size in the range of from 50 μm to 500 μm.

13. The process according to claim 1, wherein the process is employed for producing microcarrier beads coated with the gelatine-like protein in bioreactors optionally with a loading of microcarrier beads in the bioreactor of from about 20 g/l to 40 g/l.

14. The process according to claim 8, wherein the gelatine-like protein comprises a single polypeptide chain and the uniform molecular weight is within 2% of a selected molecular weight, the selected molecular weight being more than 60 kDa and less than about 150 kDa.

15. The process according to claim 7, wherein the proportion of gelatine-like protein having a uniform molecular weight within 2% of a selected molecular weight is selected from the group consisting of more than 85%, more than 95%, and at least 98%.

* * * * *

SEQUENCE LISTING

```
<160> NUMBER OF SEQ ID NOS: 1

<210> SEQ ID NO 1
<211> LENGTH: 617
<212> TYPE: PRT
<213> ORGANISM: Homo sapiens

<400> SEQUENCE: 1

Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
                85                  90                  95
```

-continued

```
Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
            115                 120                 125

Arg Gly Val Pro Gly Pro Pro Gly Ala Val Gly Pro Ala Gly Lys Asp
            130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
                165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
            195                 200                 205

Glu Pro Gly Pro Thr Gly Leu Pro Gly Pro Pro Gly Glu Arg Gly Gly
            210                 215                 220

Pro Gly Ser Arg Gly Phe Pro Gly Ala Asp Gly Val Ala Gly Pro Lys
225                 230                 235                 240

Gly Pro Ala Gly Glu Arg Gly Ser Pro Gly Pro Ala Gly Pro Lys Gly
                245                 250                 255

Ser Pro Gly Glu Ala Gly Arg Pro Gly Glu Ala Gly Leu Pro Gly Ala
            260                 265                 270

Lys Gly Leu Thr Gly Ser Pro Gly Ser Pro Gly Pro Asp Gly Lys Thr
            275                 280                 285

Gly Pro Pro Gly Pro Ala Gly Gln Asp Gly Arg Pro Gly Pro Pro Gly
            290                 295                 300

Pro Pro Gly Ala Arg Gly Gln Ala Gly Val Met Gly Phe Pro Gly Pro
305                 310                 315                 320

Lys Gly Ala Ala Gly Glu Pro Gly Lys Ala Gly Glu Arg Gly Val Pro
                325                 330                 335

Gly Pro Pro Gly Ala Val Gly Pro Ala Gly Lys Asp Gly Glu Ala Gly
            340                 345                 350

Ala Gln Gly Pro Pro Gly Pro Ala Gly Pro Ala Gly Glu Arg Gly Glu
            355                 360                 365

Gln Gly Pro Ala Gly Ser Pro Gly Phe Gln Gly Leu Pro Gly Pro Ala
            370                 375                 380

Gly Pro Pro Gly Glu Ala Gly Lys Pro Gly Glu Gln Gly Val Pro Gly
385                 390                 395                 400

Asp Leu Gly Ala Pro Gly Pro Ser Gly Pro Ala Gly Glu Pro Gly Pro
                405                 410                 415

Thr Gly Leu Pro Gly Pro Pro Gly Glu Arg Gly Gly Pro Gly Ser Arg
            420                 425                 430

Gly Phe Pro Gly Ala Asp Gly Val Ala Gly Pro Lys Gly Pro Ala Gly
            435                 440                 445

Glu Arg Gly Ser Pro Gly Pro Ala Gly Pro Lys Gly Ser Pro Gly Glu
            450                 455                 460

Ala Gly Arg Pro Gly Glu Ala Gly Leu Pro Gly Ala Lys Gly Leu Thr
465                 470                 475                 480

Gly Ser Pro Gly Ser Pro Gly Pro Asp Gly Lys Thr Gly Pro Pro Gly
                485                 490                 495

Pro Ala Gly Gln Asp Gly Arg Pro Gly Pro Pro Gly Pro Pro Gly Ala
            500                 505                 510
```

-continued

```
Arg Gly Gln Ala Gly Val Met Gly Phe Pro Gly Pro Lys Gly Ala Ala
            515                 520                 525

Gly Glu Pro Gly Lys Ala Gly Glu Arg Gly Val Pro Gly Pro Pro Gly
        530                 535                 540

Ala Val Gly Pro Ala Gly Lys Asp Gly Glu Ala Gly Ala Gln Gly Pro
545                 550                 555                 560

Pro Gly Pro Ala Gly Pro Ala Gly Glu Arg Gly Glu Gln Gly Pro Ala
                565                 570                 575

Gly Ser Pro Gly Phe Gln Gly Leu Pro Gly Pro Ala Gly Pro Pro Gly
            580                 585                 590

Glu Ala Gly Lys Pro Gly Glu Gln Gly Val Pro Gly Asp Leu Gly Ala
            595                 600                 605

Pro Gly Pro Ser Gly Pro Ala Gly Gly
            610                 615
```